United States Patent
Jung et al.

(10) Patent No.: US 11,554,151 B2
(45) Date of Patent: Jan. 17, 2023

(54) **COMPOSITION CONTAINING *PERILLA FRUTESCENS* FERMENTED EXTRACT FOR PREVENTION, ALLEVIATION, OR TREATMENT OF SLEEP DISORDER**

(71) Applicant: AJOU UNIVERSITY INDUSTRY-ACADEMIC COOPERATION FOUNDATION, Suwon-si (KR)

(72) Inventors: Yi Sook Jung, Yongin-si (KR); Tae Ho Kim, Pyeongtaek-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 0 days.

(21) Appl. No.: 16/767,839

(22) PCT Filed: Nov. 23, 2018

(86) PCT No.: PCT/KR2018/014558
§ 371 (c)(1),
(2) Date: May 28, 2020

(87) PCT Pub. No.: WO2019/107844
PCT Pub. Date: Jun. 6, 2019

(65) Prior Publication Data
US 2020/0376063 A1    Dec. 3, 2020

(30) Foreign Application Priority Data

Nov. 30, 2017  (KR) .................. 10-2017-0163476
Jul. 6, 2018  (KR) .................. 10-2018-0078853

(51) Int. Cl.
*A61K 36/535* (2006.01)
*A23L 33/105* (2016.01)

(52) U.S. Cl.
CPC .......... *A61K 36/535* (2013.01); *A23L 33/105* (2016.08); *A61K 2236/19* (2013.01); *A61K 2236/333* (2013.01)

(58) Field of Classification Search
None
See application file for complete search history.

(56) References Cited

U.S. PATENT DOCUMENTS

2015/0224159 A1   8/2015  Lo et al.

FOREIGN PATENT DOCUMENTS

| CN | 1765267 A | 5/2006 |
|---|---|---|
| CN | 105963426 A | 9/2016 |
| CN | 106987307 A | 7/2017 |
| JP | 2006-036696 A | 2/2006 |
| JP | 2006-061091 A | 3/2006 |
| JP | 2006-062998 A | 3/2006 |
| KR | 2003066566 A * | 7/2003 |
| KR | 10-2013-0099247 A | 9/2013 |
| KR | 10-2015-0049755 A | 5/2015 |

OTHER PUBLICATIONS

Kim et al. (2007) The Journal of Microbiology, vol. 45, No. 2: 128-132. (Year: 2007).*
Dordevic et al. (2010) Food Chemistry 119: 957-963. (Year: 2010).*
Hur et al. (2014) Food Chemistry 160: 346-356. (Year: 2014).*
Huynh et al. (2014) Int. J. Mol. Sci. 15: 19369-19388. (Year: 2014).*
Shen et al. (2018) J. Agric. Food Chem. 66, 2735-2741. (Year: 2018).*
International Search Report for PCT/KR2018/014558 dated Apr. 16, 2019 [PCT/ISA/210].
Gisho Honda et al., "Isolation of Sedative Principles from Perilla frutescens", Chem. Pharma. Bull. vol. 34, No. 4, pp. 1986, 1672-1677, (6 pages total).
Kwon et al., "Rosmarinic Acid Potentiates Pentobarbital-Induced Sleep Behaviors and Non-Rapid Eye Movement (NREM) Sleep through the Activation of $GABA_A$-ergic Systems", Biomol Ther, vol. 25, No. 2, pp. 105-111, 2017 (7 pages total).

* cited by examiner

*Primary Examiner* — Russell G Fiebig
(74) *Attorney, Agent, or Firm* — Sughrue Mion, PLLC

(57) ABSTRACT

A pharmaceutical composition, dietary supplement, or food containing a *Perilla frutescens* fermented extract is disclosed. The composition is useful for prevention or treatment of a sleep disorder. A composition or a fiber or fragrance composition containing a *Perilla frutescens* fermented extract is also disclosed. A method for treating sleep disorder employing the pharmaceutical composition, dietary supplement, food, or the fiber or fragrance composition is disclosed.

4 Claims, 4 Drawing Sheets

COMPOSITION CONTAINING *PERILLA FRUTESCENS* FERMENTED EXTRACT FOR PREVENTION, ALLEVIATION, OR TREATMENT OF SLEEP DISORDER

GOVERNMENT SUPPORT

This invention was made, at least in part, with government support under Grant Identification ICT (2018K000277 and 2020-JDH-2-CG-1) awarded by the Commercialization Promotion Agency for R&D Outcomes (COMPA), the Ministry of Science of Republic of Korea.

CROSS REFERENCE TO RELATED APPLICATIONS

This application is a National Stage of International Application No. PCT/KR2018/014558 filed Nov. 23, 2018, claiming priority based on Korean Patent Application No. 10-2017-0163476 filed Nov. 30, 2017 and Korean Patent Application No. 10-2018-0078853 filed Jul. 6, 2018.

TECHNICAL FIELD

The present invention relates to a pharmaceutical composition or health functional food composition comprising a *Perilla frutescens* fermented extract for prevention or treatment of a sleep disorder.

In addition, the present invention relates to a composition or a fiber or fragrance composition comprising a *Perilla frutescens* fermented extract for sleep improvement.

In addition, the present invention relates to a method for treatment of a sleep disorder, the method comprising a step of administering a *Perilla frutescens* fermented extract to a patient with a sleep disorder.

In addition, the present invention relates to a use of a *Perilla frutescens* fermented extract for use in the preparation of a composition for treatment of a sleep disorder or for prevention or treatment of a sleep disorder.

BACKGROUND ART

Sleep refers to a state in which conscious activity is resting with eyes closed. This is an important step in replenishing the energy used during daytime activities and relieving fatigue accumulated by physical activity, and is simultaneously the time when most of the growth hormones required for human growth are secreted. In addition, the brain, which supervises all the physiological functions for maintaining our body's life, needs to rest in order to maintain an appropriate activity balance, and such rest occurs during sleep hours in most cases. Recently, the American Thoracic Society has recommended that adults sleep 6 to 9 hours a day.

However, sleep problems occur due to the exhausting and busy daily lives of modern people, the aging of the population, and the like, so that the number of patients receiving treatment has been increasing in recent years, and it is expected that the number will continue to increase in the future. Sleep-related disorders are directly detrimental to health, but recent studies show that the lack of sleep increases the risk of diabetes, heart disease, and obesity. In a study from the journal 'Sleep' published in 2004, women who slept on average less than five hours a night had significantly higher mortality rates than women who slept seven hours a night.

Currently, administration of sleeping drugs, tranquilizers, stress relievers, and the like is used as a general therapy to treat most of the sleep disorders. However, when these medicines are taken for a long period of 4 weeks or more, problems of dependence and drug side effects occur, and in the case of elderly people and pregnant women, the administration of the drugs described above is restricted. Therefore, there is an increasing need for the development of a drug consisting of a natural material which has few side effects and can effectively treat sleep disorders or improve sleep quality besides the aforementioned drugs.

*Perilla frutescens* is an annual plant of the Lamiaceae family, is used to treat various diseases such as coughs, sputum, pharyngolaryngitis, dyspepsia, boils, paralytic diabetes, and back pain, and is known to have antibacterial or anticancer effects.

Japanese Patent Application No. 2004-219382 relates to a composition having an action of promoting good sleep and a beverage containing the same, and includes a *Perilla frutescens* leaf extract. The patent application discloses that ingestion of the aforementioned composition has an effect of inducing good sleep, such as prolonging of sleeping time.

However, no studies and reports have been made on the effects of a composition obtained by fermenting a *Perilla frutescens* extract with a microorganism on the improvement of sleep quality such as sleep disorder treatment or sleep improvement.

DISCLOSURE

Technical Problem

Thus, the present inventors confirmed that a *Perilla frutescens* fermented extract has effects of shortening sleep latency and increasing total sleeping time, confirmed these effects are superior compared to existing drugs used for the treatment of a sleep disorder, and the like, thereby completing the present invention.

Therefore, an object of the present invention is to provide a pharmaceutical composition or health functional food composition comprising a *Perilla frutescens* fermented extract for prevention or treatment of a sleep disorder.

Another object of the present invention is to provide a composition or a fiber or fragrance composition comprising a *Perilla frutescens* fermented extract for sleep improvement.

Still another object of the present invention is to provide a method for treatment of a sleep disorder, the method comprising a step of administering a *Perilla frutescens* fermented extract to a patient with a sleep disorder.

Yet another object of the present invention is to provide a use of a *Perilla frutescens* fermented extract for use in the preparation of a composition for treatment of a sleep disorder or for prevention or treatment of a sleep disorder.

Technical Solution

To achieve the objects, the present invention may provide a pharmaceutical composition comprising a *Perilla frutescens* fermented extract for prevention or treatment of a sleep disorder.

The present invention may also provide a method for treatment of a sleep disorder, the method comprising a step of administering a *Perilla frutescens* fermented extract to a patient with a sleep disorder.

The present invention may also provide a use of a *Perilla frutescens* fermented extract for use in the preparation of a composition for treatment of a sleep disorder.

The present invention may also provide a *Perilla frutescens* fermented extract for use in the prevention or treatment of a sleep disorder.

According to a preferred exemplary embodiment of the present invention, the fermented extract may be extracted from any one or more sites selected from the group consisting of leaves, stems, flowers, fruit, and seeds of *Perilla frutescens*.

According to a preferred exemplary embodiment of the present invention, the fermented extract may be extracted with water, a $C_1$ to $C_4$ organic solvent, or a mixture thereof as a solvent, and then fermented with a fermentation strain.

According to a preferred exemplary embodiment of the present invention, the fermentation strain may be any one or more strains consisting of bacillus, lactobacillus, and yeast.

According to a preferred exemplary embodiment of the present invention, the bacillus, the lactobacillus, and the yeast may be species belonging to the Bacillus genus, the Lactobacillus genus, and the Saccharomyces genus, respectively.

According to a preferred exemplary embodiment of the present invention, the fermentation may be performed at 5° C. to 80° C. for 30 minutes to 10 days.

According to a preferred exemplary embodiment of the present invention, the sleep disorder may be any one or more selected from the group consisting of disturbance of sleep induction, deep sleep disorder, halfway awakening, early awakening, insomnia, nightmares, somnambulism, narcolepsy, abnormal behavior during sleep, hypersomnia, sleep seizures, breathing-related sleep disorder, apnea syndrome, circadian rhythm sleep disorders, parasomnia, restless leg syndrome, and periodic limb movement disorder.

The present invention may also provide a health functional food composition comprising a *Perilla frutescens* fermented extract for prevention or alleviation of a sleep disorder.

The present invention may also provide a composition comprising a *Perilla frutescens* fermented extract for sleep improvement.

According to a preferred exemplary embodiment of the present invention, the composition may be any one or more compositions selected from the group consisting of a food composition, a cosmetic composition, a dye composition, a pharmaceutical composition, and a quasi-drug composition.

The present invention may also provide a sleep aid comprising a *Perilla frutescens* fermented extract.

The present invention may also provide a fiber comprising a *Perilla frutescens* fermented extract for sleep improvement.

According to a preferred exemplary embodiment of the present invention, the fiber may be dyed with a *Perilla frutescens* fermented extract.

According to a preferred exemplary embodiment of the present invention, the fiber may be included in any one or more products selected from the group consisting of bedding, clothes, curtains, carpets, indoor shoes, towels, wallpaper, interior fabric coverings, dolls, and eye patches.

The present invention may also provide a fragrance composition comprising a *Perilla frutescens* fermented extract.

According to a preferred exemplary embodiment of the present invention, the composition may be comprised in any one or more products selected from the group consisting of perfumes, aromas, oils, fragrances, detergents, and preparations for external application to the skin.

Hereinafter, the present invention will be described in more detail.

As described above, in the related art, when a drug such as a sleeping drug or a sedative prescribed for treatment of a sleep disorder or the like is continuously administered, there is a critical point at which dependency or drug side effects occur(s). As a measure for overcoming this, there is a need for developing a composition which has excellent effects of treating a sleep disorder and the like while using plant-derived natural materials.

A *Perilla frutescens* fermented extract according to the present invention is fermented using various microomanisms such as bacillus, and has effects of significantly shortening sleep latency and significantly increasing total sleeping time, and thus is effective as a composition for prevention, alleviation, or treatment of a sleep disorder.

As used herein, "sleep disorder" is a disease relating to sleep, and refers to a condition in which sleep is disturbed by various factors. A sleep disorder may be classified according to its causes, but when it is caused by emotional factors, it is called "nonorganic sleep disorder", and when it is caused by physical factors, it is called "organic sleep disorder".

As used herein, "sleep improvement" refers to all the effects of qualitatively or quantitatively alleviating various symptoms related to the aforementioned sleep disorder and other symptoms that make it difficult to sleep smoothly.

As used herein "sleep latency" refers to the time it takes to enter deep sleep. A sleep disorder in which one falls asleep but has difficulty entering deep sleep is called "disturbance of sleep induction".

As used herein, "total sleeping time" refers to the time during which sleep is maintained.

As used herein, "*Perilla frutescens* fermented extract" means that a *Perilla frutescens* extract is first prepared, and then the extract is fermented using a fermentation strain.

Therefore, the present invention provides a pharmaceutical composition comprising a *Perilla frutescens* fermented extract for prevention or treatment of a sleep disorder.

*Perilla frutescens* is also called *Perilla frutescens* Britton var. *acuta* Kud, and is known to have antibacterial or anticancer effects. *Perilla frutescens* may also be used to cook rice used in California rolls or with sushi, and may also be used as a dye to color food or dye fabrics, and the like.

In order to prepare a *Perilla frutescens* fermented extract, a *Perilla frutescens* extract is first prepared. The *Perilla frutescens* extract may be extracted from above-ground parts such as the leaves, stems, flowers or fruit, or seeds of *Perilla frutescens*, but is preferably extracted from the above-ground parts such as the leaves, stems, flowers or fruit of *Perilla frutescens*, and is most preferably extracted from the leaves of *Perilla frutescens*. The extraction solvent may be water, a $C_1$ to $C_4$ organic solvent, or a mixture thereof, but is preferably water or a $C_1$ to $C_4$ alcohol, more preferably water, methanol, ethanol, or propanol, and most preferably water (Example 1).

As the fermentation strain which may be used to ferment the *Perilla frutescens* extract, bacillus, lactobacillus, or yeast may be used, and it is preferred to enhance the sleep improvement effect of the *Perilla frutescens* extract that the bacillus are species belonging to the *Bacillus* genus, the lactobacillus are species belonging to the *Lactobacillus* genus, and the yeast are species belonging to the *Saccharomyces* genus.

The bacillus may be any one or more *Bacillus* genus bacteria selected from the group consisting of *Bacillus subtilis*, *Bacillus thuringiensis*, *Bacillus licheniformis*, *Bacillus amyloliquefaciens*, *Bacillus stearothermophilus*, *Bacillus coagulans*, *Bacillus longum*, *Bacillus pumilus*, *Bacillus brevis*, *Bacillus circulans*, and *Bacillus polymyxa*;

the lactobacillus may be any one or more *Lactobacillus* genus bacteria selected from the group consisting of *Lactobacillus acidophilus*, *Lactobacillus casei*, *Lactobacillus gasseri*, *Lactobacillus bulgaricus*, *Lactobacillus helveticus*, *Lactobacillus fermentum*, *Lactobacillus paracasei*, *Lactobacillus plantarum*, *Lactobacillus reuteri*, *Lactobacillus rhamnosus*, and *Lactobacillus salivarius*; and the yeast may be any one or more *Saccharomyces* genus bacteria selected from the group consisting of *Saccharomyces cerevisiae*, *Saccharomyces uvarum*, *Saccharomyces ellipsoideus*, *Saccharomyces carlsbergensis*, *Saccharomyces sake*, *Saccharomyces coreanus*, *Saccharomyces lipolytica*, *Saccharomyces boulardii*, and *Saccharomyces pastorianus*.

The fermentation is carried out preferably at 5° C. to 80° C. for 30 minutes to 10 days, more preferably at 20° C. to 40° C. for 3 days to 8 days, and most preferably at 22° C. to 30° C. for 4 days to 6 days (Example 1).

The administration route of the *Perilla frutescens* fermented extract can be oral or parenteral, and in the case of parenteral administration, the *Perilla frutescens* fermented extract may be administered via a route such as topical, injection, transdermal or nasal, but the route is not limited thereto. The administration of the *Perilla frutescens* fermented extract of the present invention may alleviate various symptoms related to sleep disorders and obtain other sleep improvement effects, so that it is possible to satisfy the sleeping time recommended worldwide or desired by individuals.

The sleep disorder of the present invention means all disorders which exhibit abnormal symptoms related to sleep, but is preferably any one or more selected from the group consisting of disturbance of sleep induction, deep sleep disorder, halfway awakening, early awakening, insomnia, nightmares, somnambulism, narcolepsy, abnormal behavior during sleep, hypersomnia, sleep seizures, breathing-related sleep disorder, apnea syndrome, circadian rhythm sleep disorders, parasomnia, restless leg syndrome, and periodic limb movement disorder, but is not limited thereto.

The pharmaceutical compositions of the present invention may be in various oral or parenteral preparations. When the composition is formulated, the composition may be prepared using one or more buffers (for example, saline or PBS), antidiabetic agents, bacteriostats, chelating agents (for example, EDTA or glutathione), fillers, extenders, binders, adjuvants (for example, aluminum hydroxide), suspensions, thickeners, wetting agents, disintegrants or surfactants, diluents, or excipients.

Examples of a solid preparation for oral administration include a tablet, a pill, a powder, a granule, a capsule, and the like, and the solid preparation is prepared by mixing one or more compounds with at least one or more excipients, for example, starch (including corn starch, wheat starch, rice starch, potato starch, and the like), calcium carbonate, sucrose, lactose, dextrose, sorbitol, mannitol, xylitol, erythritol maltitol, cellulose, methyl cellulose, sodium carboxymethylcellulose and hydroxypropyl methylcellulose, gelatin, or the like. For example, a tablet or a sugar tablet may be obtained by blending an active ingredient with a solid excipient, pulverizing the resulting blend, adding a suitable auxiliary agent thereto, and then processing the resulting mixture into a granular mixture. Further, in addition to a simple excipient, lubricants such as magnesium stearate and talc are also used.

A liquid preparation for oral administration corresponds to a suspension, a liquid for internal use, an emulsion, a syrup, and the like, and the liquid preparation may include, in addition to water and liquid paraffin which are simple commonly used diluents, various excipients, for example, a wetting agent, a sweetener, a flavoring agent, a preservative, or the like. In addition, in some cases, cross-linked polyvinyl pyrrolidone, agar, alginic acid, sodium alginate, or the like may be added as a disintegrant, and an anti-coagulant, a lubricant, a wetting agent, a flavoring agent, an emulsifier, an antiseptic, and the like may be additionally added.

Preparations for parenteral administration include an aqueous sterile solution, a non-aqueous solvent, a suspension solvent, an emulsion, a freeze-dried preparation, a suppository, or the like. As the non-aqueous solvent and the suspension solvent, it is possible to use propylene glycol, polyethylene glycol, a vegetable oil such as olive oil, an injectable ester such as ethyl oleate, and the like. As a base of the suppository, it is possible to use Witepsol, Macrogol, Tween 61, cacao butter, laurin fat, glycerol, gelatin, and the like.

The pharmaceutical composition of the present invention may be administered orally or parenterally, and, when administered parenterally, may be formulated in the form of a preparation for external application to the skin; an injection administered intraperitoneally, intrarectally, intravenously, intramuscularly, subcutaneously, or intracerebroventricularly, or via cervical intrathecal injection; a transdermal administration agent; or a nasal inhaler according to a method known in the art.

The injection must be sterilized and protected from contamination by microorganisms such as bacteria and fungi. Examples of a suitable carrier for injection may be, but are not limited to, a solvent or a dispersion medium including water, ethanol, polyols (for example, glycerol, propylene glycol, liquid polyethylene glycol, and the like), mixtures thereof, and/or vegetable oils. More preferably, as a suitable carrier, it is possible to use an isotonic solution such as Hank's solution, Ringer's solution, triethanolamine-containing phosphate buffered saline (PBS) or sterile water for injection, 10% ethanol, 40% propylene glycol, and 5% dextrose, and the like. To protect the injection from microbial contamination, various antimicrobial agents and anti-fungal agents such as paraben, chlorobutanol, phenol, sorbic acid, and thimerosal may be additionally included. Furthermore, in most cases, the injection may additionally include an isotonic agent such as sugar or sodium chloride.

Examples of the transdermal administration agent include a form such as an ointment, a cream, a lotion, a gel, a solution for external use, a paste, a liniment, and an aerosol. The transdermal administration as described above means that an effective amount of an active ingredient contained in a pharmaceutical composition is delivered into the skin via local administration thereof to the skin.

In the case of a preparation for inhalation, the extract used according to the present invention may be conveniently delivered in the form of an aerosol spray from a pressurized pack or a nebulizer using a suitable propellant, for example, dichlorofluoromethane, trichlorofluoromethane, dichlorotetrafluoroethane, carbon dioxide, or other suitable gases. In the case of the pressurized aerosol, a dosage unit may be determined by providing a valve for transferring a metered amount. For example, a gelatin capsule and a cartridge for use in an inhaler or insufflator may be formulated so as to contain a powder mixture of a compound and a suitable powder base such as lactose or starch. Formulations for parenteral administration are described in the document, which is a guidebook generally known in all pharmaceutical chemistry fields (Remington's Pharmaceutical Science, 15th Edition, 1975. Mack Publishing Company, Easton, Pa. 18042, Chapter 87: Blaug, Seymour).

The pharmaceutical composition of the present invention is administered in a pharmaceutically effective amount, and the pharmaceutically effective amount refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, factors including simultaneously used drugs, and other factors well known in the medical field. The composition of the present invention may be administered as an individual therapeutic agent or in combination with other therapeutic agents, may be administered sequentially or simultaneously with therapeutic agents in the related art, and may be administered in a single dose or multiple doses. That is, the total effective amount of the composition of the present invention may be administered to a patient in a single dose or may be administered by a fractionated treatment protocol, in which multiple doses are administered over a long period of time. It is important to administer the composition in a minimum amount that can obtain the maximum effect without any side effects, in consideration of all the aforementioned factors, and this amount may be easily determined by the person skilled in the art.

A dosage of the pharmaceutical composition of the present invention varies according to the body weight, age, gender, and health status of a patient, diet, administration time, administration method, excretion rate, and the severity of a disease. A daily dosage thereof may be administered parenterally in an amount of preferably 0.01 to 200 mg, and more preferably 0.1 mg to 120 mg per 1 kg of body weight a day based on a *Perilla frutescens* fermented extract, and a daily dosage thereof may be administered orally in a single dose or multiple doses in an amount of preferably 0.01 to 200 mg, and more preferably 0.01 to 20 mg per 1 kg of body weight a day based on the *Perilla frutescens* fermented extract of the present invention. However, since the effective amount may be increased or decreased depending on the administration route, the severity of obesity, gender, body weight, age, and the like, the dosage is not intended to limit e scope of the present invention in any way.

The composition of the present invention may be used either alone or n combination with surgery, radiation therapy, hormone therapy, chemotherapy, and methods using a biological response modifier.

The pharmaceutical composition of the present invention may also be provided in the form of an external preparation including the *Perilla frutescens* fermented extract as an active ingredient. When the pharmaceutical composition for sleep improvement or for treatment of a sleep disorder according to the present invention is used as a preparation for external application to the skin, the pharmaceutical composition may additionally contain auxiliary agents typically used in the dermatology field, such as any other ingredients typically used in the preparation for external application to the skin, such as a fatty material, an organic solvent, a solubilizing agent, a thickener and a gelling agent, a softener, an antidiabetic agent, a suspending agent, a stabilizer, a foaming agent, a fragrance, a surfactant, water, an ionic emulsifier, a non-ionic emulsifier, a filler, a metal ion blocking agent, a chelating agent, a preservative, a vitamin, a blocking agent, a wetting agent, an essential oil, a dye, a pigment, a hydrophilic active agent, a lipophilic active agent, or a lipid vesicle. In addition, the ingredients may be introduced in an amount generally used in the dermatology field.

When the pharmaceutical composition for sleep improvement or for treatment of a sleep disorder according to the present invention is provided as a preparation for external application to the skin, the pharmaceutical composition may be in the form of a formulation such as an ointment, a patch, a gel, a cream, and an aerosol, but is not limited thereto.

In addition, the present invention provides a health functional food composition comprising a *Perilla frutescens* fermented extract for prevention or alleviation of a sleep disorder.

Since the *Perilla frutescens* fermented extract s the same as that used for the pharmaceutical composition, the description thereof will be replaced with the above description thereof.

The type of health functional food is not particularly limited. Examples thereof include drinks, meats, sausages, bread, biscuits, rice cake, chocolate, candies, snacks, confectioneries, pizza, instant noodles, other noodles, gum, dairy products including ice cream, various soups, drinking water, alcoholic beverages and vitamin complexes, milk products and dairy products, and the like, and include all health functional foods in a typical sense.

The *Perilla frutescens* fermented extract of the present invention may be added as is to food or may be used together with other foods or food ingredients and may be appropriately used by a typical method. The mixing amount of the active ingredient may be suitably determined depending on its purpose of use (for prevention or alleviation). In general, the amount of the compound in the health food may be 0.1 to 90 parts by weight of the total food weight. However, in the case of long-term intake for the purpose of health and hygiene, or for the purpose of controlling health, the amount may be equal to or less than the above range, and the effective ingredient may be used in an amount equal to or more than the above range due to no problem in terms of safety.

Other ingredients are not particularly limited, except that the health functional beverage composition of the present invention contains the compound of the present invention as an essential ingredient at an indicated ratio, and the health functional beverage composition of the present invention may contain various flavoring, agents like a typical beverage, natural carbohydrates, and the like as an additional ingredient. Examples of the above-described natural carbohydrates include typical sugars such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, and erythritol. As the flavoring agent except for those described above, a natural flavoring agent (thaumatin, a stevia extract (for example, rebaudioside A, glycyrrhizin and the like), and a synthetic flavoring agent (saccharin, aspartame and the like) may be advantageously used. The proportion of the natural carbohydrate is generally about 1 to 20 g, and preferably about 5 to 12 g per 100 g of the composition of the present invention.

The *Perilla frutescens* fermented extract of the present invention may contain various nutrients, vitamins, minerals (electrolytes), flavoring agents such as synthetic flavoring agents and natural flavoring agents, colorants and fillers (cheese, chocolate, and the like), pectic acid and salts thereof, alginic acid and salts thereof, organic acids, protective colloid thickeners, pH adjusting agents, stabilizers, antiseptics, glycerin, alcohols, carbonating agents used in a carbonated beverage, or the like, in addition to those described above in addition, the *Perilla frutescens* fermented extract of the present invention may contain fruit pulp for the preparation of natural fruit juices and fruit juice beverages and vegetable beverages. These ingredients may be used either alone or in combinations thereof. The proportion of these additives is not significantly important, but is generally selected within a range of 0.1 to 20 parts by weight per 100 parts by weight of the *Perilla frutescens* fermented extract of the present invention.

In addition, the present invention provides a composition comprising a *Perilla frutescens* fermented extract for sleep improvement.

Since the *Perilla frutescens* fermented extract is the same as that used for the pharmaceutical composition, the description thereof will be replaced with the above description thereof.

The composition of the present invention is preferably any one or more compositions selected from the group consisting of a food composition, a cosmetic composition, a dye composition, a pharmaceutical composition, and a quasi-drug composition, but is not limited thereto.

When the composition of the present invention is formulated into a cosmetic composition, the content of the *Perilla frutescens* fermented extract is 0.0001 to 10 wt %, preferably 0.01 to 5.0 wt %, based on the total weight of the cosmetic composition. In order to achieve the minimum effect of alleviating or preventing skin cancer, the content of the *Perilla frutescens* fermented extract is preferably no less than the above minimum value, and the content of the *Perilla frutescens* fermented extract is preferably no more than the above maximum value considering reduced usability and applicability to various formulations according to excess addition. In this case, it is preferred that the content of the *Perilla frutescens* fermented extract is appropriately adjusted within the above range according to the content of the ingredients contained in the formulation or cosmetic composition.

The ingredients included in the cosmetic composition of the present invention include ingredients typically used for the cosmetic composition in addition to the *Perilla frutescens* fermented extract as an active ingredient, and includes, for example, a typical adjuvant such as an antioxidant, a stabilizer, a solubilizer, a vitamin, a pigment, and a flavoring agent, and a carrier.

The cosmetic composition of the present invention may be prepared into any typical formulation prepared in the art, and may be formulated into a cosmetic such as, for example, softening lotion, astringent lotion, nourishing lotion, nourishing cream, massage cream, essence, eye cream, eye essence, cleansing cream, cleansing foam, cleansing water, packs, gel, powder, body lotion, body cream, body oil, and body essence.

When the formulation of the present invention is a paste, a cream or a gel, an animal oil, a vegetable oil, a wax, paraffin, starch, tragacanth, a cellulose derivative, a polyethylene glycol, silicone, bentonite, silica, talc, zinc oxide, or the like may be used as a carrier ingredient.

When the formulation of the present invention is a powder or a spray, lactose, talc, silica, aluminum hydroxide, calcium silicate, or a poly amide powder may be used as the carrier ingredient, and in particular, when the formulation of the present invention is a spray, the formulation may additionally include a propellant such as chlorofluorohydrocarbon, propane/butane or dimethyl ether.

When the formulation of the present invention is a solution or an emulsion, a solvent, a solubilizer or an emulsifier is used as the carrier ingredient, and examples thereof include water, ethanol, isopropanol, ethyl carbonate, ethyl acetate, benzyl alcohol, benzyl benzoate, propylene glycol, 1,3-butylglycol oil, glycerol aliphatic esters, polyethylene glycol or fatty acid esters of sorbitan.

When the formulation of the present invention is a suspension, a liquid diluent such as water, ethanol or propylene glycol, a suspension such as ethoxylated isostearyl alcohol, polyoxyethylene sorbitol ester and polyoxyethylene sorbitan ester, microcrystalline cellulose, aluminum metahydroxide, bentonite, agar, tragacanth, or the like may be used as the carrier ingredient.

When the formulation of the present invention is a surfactant-containing cleanser, an aliphatic alcohol sulfate, an aliphatic alcohol ether sulfate, sulphosuccinic acid monoester, isethionate, an imidazolinium derivative, methyltaurate, a sarcosinate, fatty acid amide ether sulfate, alkylamido betaine, an aliphatic alcohol, fatty acid glyceride, fatty acid diethanolamide, a vegetable oil, a lanolin derivative, an ethoxylated glycerol fatty acid ester, or the like may be used as the carrier ingredient.

In addition, the present invention provides a sleep aid including a *Perilla frutescens* fermented extract.

Since the *Perilla frutescens* fermented extract is the same as that used for the pharmaceutical composition, the description thereof will be replaced with the above description thereof.

The sleep aid, unlike a sleeping drug, refer to a generic drug having a sleep-inducing or sedative effect, which may be purchased without a prescription from a professional.

In addition, the present invention provides a fiber comprising a *Perilla frutescens* fermented extract for sleep improvement.

Since the *Perilla frutescens* fermented extract is the same as that used for the pharmaceutical composition, the description thereof will be replaced with the above description thereof.

The fiber of the present invention refers to all fibers exhibiting the sleep improvement effect due to the *Perilla frutescens* fermented extract, such as a fiber prepared using the *Perilla frutescens* fermented extract as a raw material, a fiber dyed using the *Perilla frutescens* fermented extract as a dye, or a fiber in which the *Perilla frutescens* fermented extract is attached to the fiber surface by spraying and the like, and is preferably a fiber dyed using the *Perilla frutescens* fermented extract as a dye.

The fiber may be used in any of the products capable of affecting the sleeping environment, and is preferably included in any one or more products selected from the group consisting of bedding, clothes, curtains, carpets, indoor shoes, towels, wallpaper, interior fabric coverings, dolls, and eye patches, but is not limited thereto.

The bedding refers to bedlinen and a sleeping pad (a quilt, a sleeping mat), pillows, cushions, and the like required to sleep, the clothes refer to pajamas, underwear or socks worn during sleeping, and the interior fabric coverings refer to fabric coverings used to cover and store furniture, such as chairs or desks, decorations, and appliances, due to contamination or other reasons, but these products are not limited thereto.

In addition, the present invention provides a fragrance composition comprising a *Perilla frutescens* fermented extract.

Since the *Perilla frutescens* fermented extract is the same as that used for the pharmaceutical composition, the description thereof will be replaced with the above description thereof.

The fragrance refers to all materials used to produce a scent, such as an aroma.

The fragrance composition may be included without limitation as long as the fragrance composition is a product used for a use of producing a scent while being capable of exhibiting the sleep improvement effect due to the *Perilla frutescens* fermented extract, but is preferably included in any one or more products selected from the group consisting of perfumes, fragrant herbs, oils, fragrances, detergents, and preparations for external application to the skin. The preparation for external application to the skin includes, all products necessary for bathing, such as soap, a face wash or a bathing agent, but is not limited thereto.

The amount of the *Perilla frutescens* fermented extract included in the products may be appropriately adjusted and included in order to achieve a desired effect according to a conventional technique in the art.

In addition, the present invention provides a method for treatment of a sleep disorder, the method comprising a step of administering a *Perilla frutescens* fermented extract to a patient with a sleep disorder.

Since the *Perilla frutescens* fermented extract and the sleep disorder are the same as the *Perilla frutescens* fermented extract and the sleep disorder of the pharmaceutical composition, the description thereof will be replaced with the above description thereof.

In addition, the present invention provides a use of a *Perilla frutescens* fermented extract for use in the preparation of a composition for treatment of a sleep disorder.

Since the *Perilla frutescens* fermented extract and the sleep disorder are the same as the *Perilla frutescens* fermented extract and the sleep disorder of the pharmaceutical composition, the description thereof will be replaced with the above description thereof.

In addition, the present invention provides a *Perilla frutescens* fermented extract for use in the prevention or treatment of a sleep disorder.

Since the *Perilla frutescens* fermented extract and the sleep disorder are the same as the *Perilla frutescens* fermented extract and the sleep disorder of the pharmaceutical composition, the description thereof will be replaced with the above description thereof.

Advantageous Effects

Therefore, in the present invention, the *Perilla frutescens* fermented extract, compared with an unfermented *Perilla frutescens* extract, significantly shortens sleep latency and significantly increases total sleeping time, and thus the *Perilla frutescens* fermented extract is effective as a composition for prevention, alleviation, or treatment of a sleep disorder or for sleep improvement, and can be also effectively used in a treatment method for a sleep disorder.

MODES OF THE INVENTION

Hereinafter, the present invention will be described in more detail through Examples. These Examples are only for exemplifying the present invention, and it should be obvious to a person with ordinary skill in the art that the scope of the present invention is not to be interpreted as being limited by these Examples.

Example 1

Preparation of *Perilla frutescens* Extract and Fermented Product Thereof

*Perilla frutescens* leaves were subjected to hot water extraction at 80° C. and sterilized at 121° C. for 20 minutes (*Perilla*-W). A *Perilla frutescens* fermented extract was prepared by fermenting the sterilized *Perilla frutescens* hot water extract with a bacillus, lactobacillus, or yeast.

Specifically, after *Bacillus subtilis* as one species of *Bacillus*, *Lactobacillus rhamnosus* as one species of *Lactobacillus*, or *Saccharomyces cerevisiae* as the yeast was each inoculated into the *Perilla frutescens* extract, fermented extracts of a *Perilla frutescens Bacillus subtilis* fermented product (*Perilla*-B), a *Perilla frutescens Lactobacillus rhamnosus* fermented product (*Perilla*-L), and a *Saccharomyces cerevisiae* fermented product (*Perilla*-S) were prepared by fermenting the one species for 5 days while being subjected to shaking culture at 140 rpm in an environment of a temperature of 25° C. and a humidity of 80%.

Example 2

Sleep Improvement Effects of *Perilla frutescens* Fermented Extract

<2-1> Comparison of sleep improvement effects with existing sedatives

The sleep improvement effects of the *Perilla frutescens* fermented extract and conventionally sold sedatives were intended to be confirmed from comparison of sleep latency and total sleeping time.

Specifically, 0.9% physiological saline, 10 mg/kg of the *Perilla frutescens* extract (*Perilla*-W) or fermented extract thereof (*Perilla*-B) prepared in [Example 1], and 1 mg/kg of diazepam (Myung In Pharm. Co., Ltd.) were each orally administered to ICR mice (OrientBio). 30 minutes after the administration of the test materials, 45 mg/kg of a nerve stabilizer pentobarbital (HANLIM PHARM. Co., Ltd.) was intraperitoneally administered to induce sleep. After the administration of pentobarbital, the time required to go into deep sleep (sleep latency) and the total sleep maintenance time (total sleeping time) were measured for each test material administration group. Physiological saline and diazepam were used as a control and a positive control, respectively.

Figure 1:
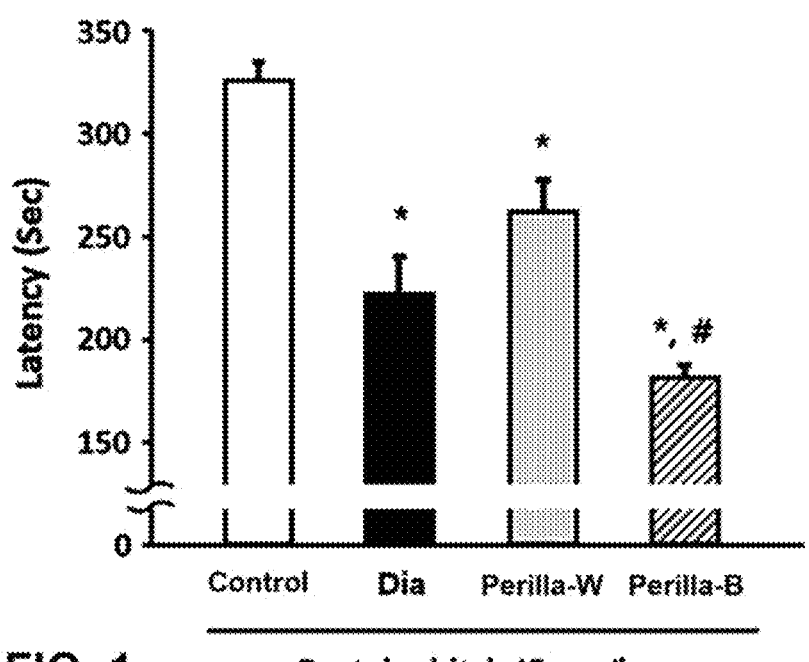
FIG. 1 illustrates the measurement results of sleep latency after inducing sleep by administering pentobarbital to rats to which a *Perilla frutescens* extract (*Perilla*-W) or a *Perilla frutescens* fermented extract (*Perilla*-B) was administered. Physiological saline was administered to a control, and diazepam was administered to Dia (positive control). It could be confirmed that when the *Perilla frutescens* extract was administered, sleep latency was the shortest, which was a value significantly decreased compared to the *Perilla frutescens* extract or the positive control group.

As a result, as illustrated in [FIG. 1], it was confirmed that when the *Perilla*-W was administered, the sleep latency (261 seconds) of the *Perilla*-W-administered group was reduced by about 20% compared to the sleep latency (325 seconds) of the control, and the sleep latency (180 seconds) of the *Perilla*-B-administered group was reduced by about 45% compared to the sleep latency of the control, and thus was more significantly reduced compared to the *Perilla*-W-administered group. In particular, a significant effect was confirmed by confirming that the *Perilla frutescens* fermented extract exhibited a sleep latency reduced by 10% or more compared to when the positive control diazepam was used (220 seconds).

Figure 2:
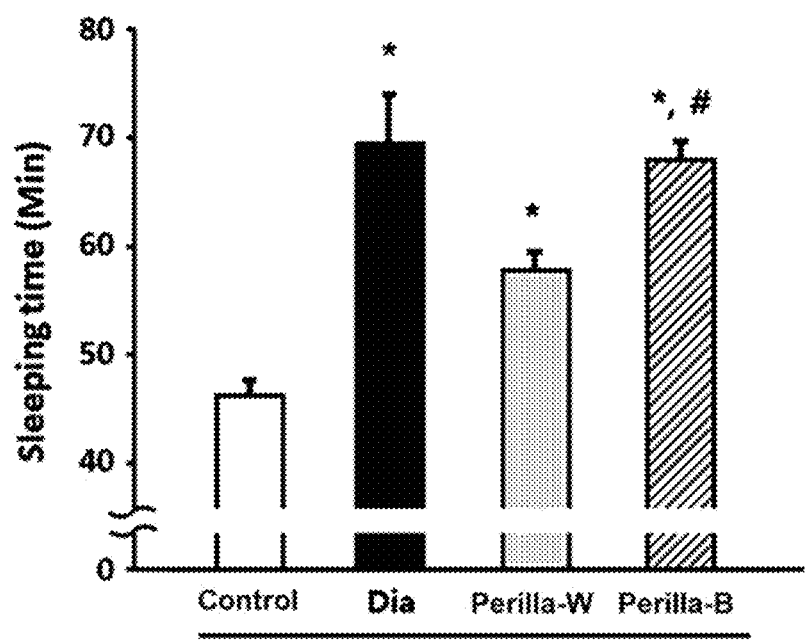
FIG. 2 illustrates the measurement results of total sleeping time after inducing sleep by administering pentobarbital to rats to which a *Perilla frutescens* extract (*Perilla*-W) or a *Perilla frutescens* fermented extract (*Perilla*-B) was administered. Physiological saline was administered to a control, and diazepam was administered to Dia (positive control). It could be confirmed that when the *Perilla frutescens* fermented extract was administered, total sleeping time was significantly increased compared to the *Perilla frutescens* extract.

In addition, as illustrated in [FIG. 2], it was confirmed that compared to the total sleeping time (46 minutes) of the control, the total sleeping time was increased by about 123% (57 minutes) when the *Perilla*-W was administered, and the total sleeping time was increased by about 138% (68 minutes) when the *Perilla*-B was administered, and thus was more significantly increased compared to that of the *Perilla*-W-administered group.

<2-2> Comparison of Sleep Improvement Effects Per Fermentation Strain

It was intended to confirm whether there is a difference in sleep improvement effects between fermentation strains fermenting the *Perilla frutescens* extract. As the fermentation strain, a bacillus, lactobacillus, or yeast was used.

Specifically, sleep latency and total sleeping time ere measured in the same manner as in Example <2-1> using 0.9% physiological saline and 10 mg/kg of the *Perilla frutescens* extract (*Perilla*-W) or fermented extract thereof (*Perilla*-B, *Perilla*-L, and *Perilla*-S) prepared in [Example 1].

Figure 3:
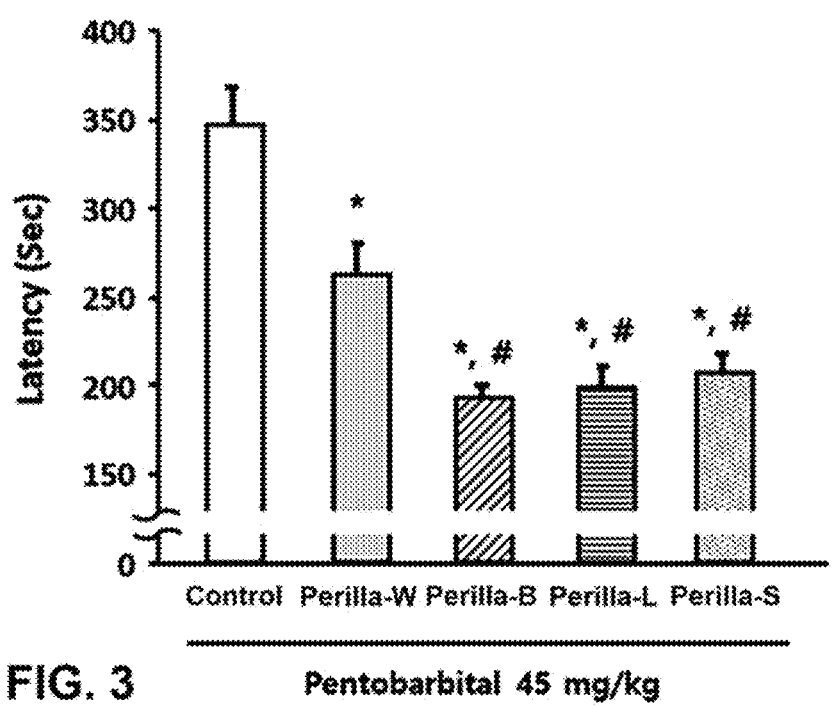
FIG. 3 illustrates the measurement results of sleep latency after inducing sleep by administering pentobarbital to rats to which a *Perilla frutescens* extract (*Perilla*-W) or a *Perilla frutescens* fermented extract (*Perilla*-B, *Perilla*-L, and *Perilla*-S) was administered. Physiological saline was administered to a control. It could be confirmed that when the *Perilla frutescens* extracts were each administered, sleep latency was significantly decreased compared to the *Perilla frutescens* extract.

As a result, as illustrated in [FIG. 3], compared to the sleep latency (350 seconds) of the control, the sleep latency of the *Perilla*-W-administered group was reduced by about 25% (261 seconds). It was shown that the sleep latency was reduced by about 49% (180 seconds), about 44% (198 seconds), and about 42% (206 seconds) in the case of administration of *Perilla frutescens* fermented extracts *Perilla*-B, *Perilla*-L, and *Perilla*-S, respectively. That is, it could be confirmed that when the *Perilla frutescens* fermented extracts were administered, sleep latency was significantly shortened compared to when the *Perilla frutescens* extract was administered, and among them, the fermentation case using a bacillus was best in effect.

Figure 4:
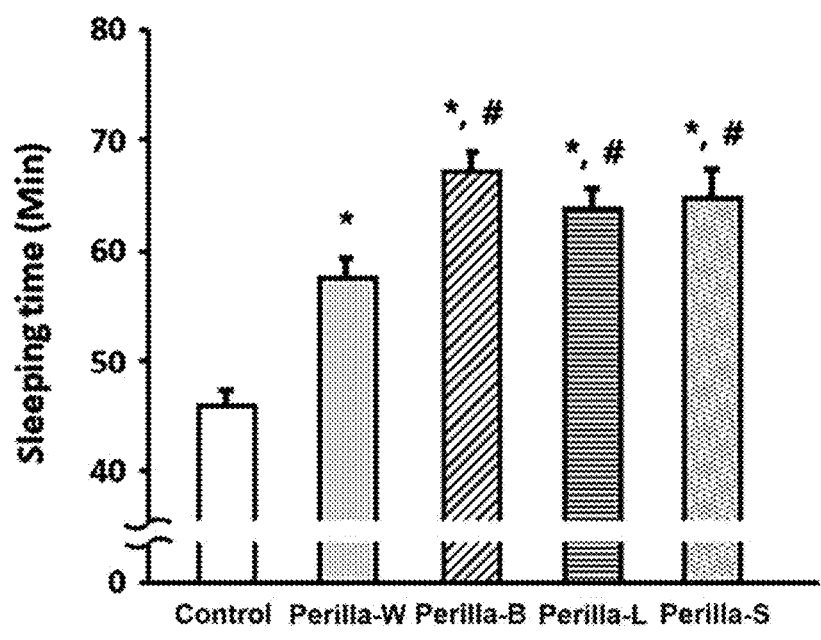
FIG. 4 illustrates the measurement results of total sleeping time after inducing sleep by administering pentobarbital to rats to which a *Perilla frutescens* extract (*Perilla*-W) or a *Perilla frutescens* fermented extract (*Perilla*-B, *Perilla*-L, and *Perilla*-S) was administered. Physiological saline was administered to a control. It could be confirmed that when the *Perilla frutescens* extracts were each administered, total sleeping time was significantly increased compared to the *Perilla frutescens* extract.

In addition, as illustrated in [FIG. 4], it was shown that when the *Perilla*-W was administered, the total sleeping time was increased by about 123% (57 minutes) compared to the total sleeping time (46 minutes) of the control, and it was shown that in the case of administration of *Perilla frutescens* fermented extracts *Perilla*-B, *Perilla*-L, and *Perilla*-S, the total sleeping time was increased by about 148% (68 minutes), about 139% (64 minutes), and about 141% (65 minutes), respectively compared to the total sleeping time of the control. That is, it could be confirmed that when the *Perilla frutescens* fermented extracts were administered, total sleeping time was significantly increased compared to when the *Perilla frutescens* extract was administered, and among them, the fermentation case using a bacillus was best in effect.

Preparation Example

1. Preparation of Health Functional Beverage

| | |
|---|---|
| Vitamins | 0.5 wt % |
| Dietary fiber | 4.0 wt % |
| Liquid fructose | 93.0 wt % |
| Emulsifier | 1.0 wt % |
| Flavor | 0.5 wt % |
| *Perilla frutescens* fermented extract | 1.0 wt % |

The composition was mixed with purified water such that the total volume became 50 ml. A final mixed solution obtained by allowing the mixed solution to pass through a 2 to 3 μm filter to remove suspended matter was sterilized at 90 to 93° C. for 15 to 20 seconds and filled in a 50 ml bottle and sterilized at 80 to 85° C. for 15 to 20 minutes, thereby completing a health functional beverage product.

2. Preparation of Lotion

| | |
|---|---|
| Hydroxyethylene cellulose (2% aqueous solution) | 12.0 wt % |
| Xanthan gum (2% aqueous solution) | 2.0 wt % |
| 1,3-butylene glycol | 6.0 wt % |
| Glycerin | 4.0 wt % |
| Sodium hyaluronate (1% aqueous solution) | 5.0 wt % |
| Ion exchanged water | 73.0 wt % |
| *Perilla frutescens* fermented extract | 3.0 wt % |

A lotion was prepared by a typical lotion preparation method.

3. Preparation of Fragrance

| | |
|---|---|
| 95% ethanol | 65.0 to 75.0 wt % |
| *Perilla frutescens* fermented extract | 25.0 to 35.0 wt % |

After the ethanol and the *Perilla frutescens* fermented extract were mixed, a fragrance was prepared by stirring the resulting mixture at room temperature for 12 to 20 minutes.

4. Preparation of Bathing Agent

| | |
|---|---|
| Sodium hydrogen carbonate | 70.0 wt % |
| Anhydrous sodium sulfate | 29.0 wt % |
| *Perilla frutescens* fermented extract | 1.0 wt % |

After the sodium bicarbonate and anhydrous sodium sulfate were stirred with a V-type mixer until the mixture became uniform, the *Perilla frutescens* fermented extract was added thereto, and the resulting mixture was sufficiently stirred until the mixture again became uniform, thereby preparing a bathing agent.

INDUSTRIAL APPLICABILITY

Therefore, in the present invention, the *Perilla frutescens* fermented extract, compared with an unfermented *Perilla frutescens* extract, significantly shortens sleep latency and significantly increases total sleeping time, and thus the *Perilla frutescens* fermented extract is effective as a composition for prevention, alleviation, or treatment of a sleep disorder or for sleep improvement, and can be also effectively used in a treatment method for a sleep disorder, so that the present invention is highly industrially applicable.

The invention claimed is:

1. A method for treatment of a sleep disorder, the method comprising a step of administering an effective amount of *Perilla frutescens* fermented extract to a patient with a sleep disorder, wherein the *Perilla frutescens* fermented extract is obtained by
    (a) extracting *Perilla frutescens* with water, a $C_1$ to $C_4$ alcohol, or a mixture thereof as an extraction solvent in an extraction solution,
    (b) fermenting the extraction solution with a microorganism comprising any one or more microorganisms selected from the group consisting of *Bacillus subtilis*, *Lactobacillus rhamnosus*, and *Saccharomyces cerevisiae*.

2. The method of claim 1, wherein the extract of *Perilla frutescens* is obtained from any one or more selected from the group consisting of leaves, stems, flowers, fruit, and seeds of *Perilla frutescens*.

3. The method of claim 1, wherein the fermentation is performed at 5° C. to 80° C. for 30 minutes to 10 days.

4. The method of claim 1, wherein the sleep disorder is any one or more selected from the group consisting of disturbance of sleep induction, deep sleep disorder, halfway awakening, early awakening, insomnia, nightmares, somnambulism, narcolepsy, abnormal behavior during sleep, hypersomnia, sleep seizures, breathing-related sleep disorder, apnea syndrome, circadian rhythm sleep disorders, parasomnia, restless leg syndrome, and periodic limb movement disorder.

* * * * *